United States Patent
Kelly (10) Patent No.: US 6,454,437 B1
(45) Date of Patent: Sep. 24, 2002

(54) RING LIGHTING

(76) Inventor: William Kelly, Birchfield House, Carrigaline, County Cork (IE)

(*) Notice: Subject to any disclaimer, the term of this patent is extended or adjusted under 35 U.S.C. 154(b) by 0 days.

(21) Appl. No.: 09/628,351

(22) Filed: Jul. 28, 2000

(30) Foreign Application Priority Data

Jul. 28, 1999 (IE) .............................................. 990646
Dec. 13, 1999 (IE) .............................................. 991032

(51) Int. Cl.[7] .......................... F21V 5/00; F21V 21/00; F21V 1/00
(52) U.S. Cl. ........................ 362/246; 362/249; 362/235; 362/252; 359/287; 359/387
(58) Field of Search .............................. 362/249, 235, 362/252, 800, 326, 335, 244, 230, 231, 246; 359/287, 387

(56) References Cited

U.S. PATENT DOCUMENTS

| | | | |
|---|---|---|---|
| 3,875,456 A | 4/1975 | Kano et al. .................. 313/501 |
| 4,567,551 A | 1/1986 | Choate ........................ 362/398 |
| 4,666,269 A | * 5/1987 | Nakamura et al. ........... 351/212 |
| 4,787,903 A | 11/1988 | Grendahl ........................ 623/6 |
| 4,969,037 A | 11/1990 | Poleschinski ............... 358/106 |
| 5,038,258 A | * 8/1991 | Koch et al. .................. 362/237 |
| 5,580,163 A | 12/1996 | Johnson, III ................ 362/285 |
| 5,690,417 A | * 11/1997 | Polidor et al. .............. 362/244 |
| 5,803,579 A | * 9/1998 | Turnbull et al. ........... 362/83.1 |
| 5,822,053 A | * 10/1998 | Thrailkill .................... 356/237 |
| 5,897,195 A | 4/1999 | Choate ......................... 362/33 |
| 6,005,024 A | * 12/1999 | Anders et al. ............... 523/172 |
| 6,033,087 A | * 3/2000 | Shozo et al. ................. 362/244 |

FOREIGN PATENT DOCUMENTS

EP 0367241 A2 5/1990

OTHER PUBLICATIONS

Patent Abstracts of Japan, vol. 1999, No. 4, & JP 11 002598 A (SHIMU:KK), Jan. 6, 1999.
Patent Abstracts of Japan, vol. 1999, No. 8 & JP 11 066937 A (T B OPT KK), Mar. 9, 1999.
Patent Abstracts of Japan, vol. 12, No. 106 & JP 62 235787 A (KOITO MFG CO LTD), Oct. 15, 1987.
Patent Abstracts of Japan, vol. 8, No. 163 & JP 59 060327 A (Matsushita Denko KK), Apr. 6, 1984.

* cited by examiner

Primary Examiner—Sandra O'Shea
Assistant Examiner—Jacob Y. Choi
(74) Attorney, Agent, or Firm—Jacobson Holman, PLLC (57) ABSTRACT

An illuminator has a printed circuit board supporting a ring of light emitting diodes (LEDs). An annular Fresnel lens and the board are both mounted in a housing having a central though-hole for a camera field of view. The lens mixes light from the LEDs in the tangential direction and it also controls spread in the radial direction so there is uniform illumination over a target plane. Any individual point on the target plane receives illumination from over 25% of the light sources. The illuminator is thus particularly effective, compact, and suitable for a wide range of industrial applications. Choice of lens and the spatial arrangement allows versatility. The illuminator design is easily scaleable by changing the size and spacing between the light sources.

28 Claims, 9 Drawing Sheets

+ — Colour 1
□ — Colour 2
△ — Colour 3

RING LIGHTING

FIELD OF THE INVENTION

The present invention relates to illuminators used in industrial instrumentation in which it is desired to illuminate an object which is being inspected by a sensor or camera. An example is the illumination of objects on a production line which are being inspected by a machine vision system.

PRIOR ART DISCUSSION

A typical machine vision system consists of an illuminator, a camera, and a control system for enabling the illuminator and camera in combination to capture an image of the object which is under inspection and for processing the image and initiating the desired action. The action may be marking the product as acceptable or rejected. The illuminator is an important part of the system, and properties of the illumination such as its brightness, its uniformity, its angle of incidence, its colour, and its degree of collimation can have a significant influence on the overall performance of the complete vision system. Additionally, the physical size of the illuminator is very important, as for some vision systems there is very little physical space available. For example, it may need to be located within a camera housing. Several types of illuminator have been used with machine vision systems, for example incandescent bulbs, fluorescent tubes, lasers, Xenon flash tubes, halogen bulbs combined with fibre light guides, and light emitting diodes (LEDs). Due to their relative cheapness, physically small size, long lifetime, fast switching speed and reasonable efficiency, LEDs have become increasingly popular.

FIG. A illustrates the main features of a typical prior art ring illuminator, such as for example displayed at the Volpi™ website, or in the Electronic Imaging Catalog of Edmunds Industrial Optics Inc™. The illuminator consists of an arrangement of light emitting diodes arranged either within a housing, or on a printed circuit board within a housing, with a hole in the centre of the housing and board through which a camera or sensor can view the objects which are being illuminated. Each LED is in its own package, usually lensed so as to provide a "viewing angle" of between 4 degrees and 120 degrees. By viewing angle is meant the full width angle measurement in the far field at the half power points of the light which is being emitted from the package. In general, the light from these packages has a cross-sectional profile which is such that it can not be described by a smooth mathematical function such as a Gaussian function, but has undesirable intensity variations caused by the structure of the LED chip and/or by the arrangement of the LED within the optical elements of the package. It can be seen additionally from FIG. A that there is the potential for a lot of structure (non-uniformity) in the illumination pattern which is produced when these packaged LEDs are used to make a ring illuminator depending upon how well the beams from the individual LEDs mix. This can be improved by adding diffuser material either within the individual LED packages or on the exterior of the housing of the illuminator, but the effect in both circumstances is to reduce the efficiency of the system. It can also be seen from FIG. A that the overall volume of the illuminator is very much determined by the size of the individual diode packages, which are typically several millimeters in diameter.

A problem with such illuminators is that the pointing accuracy of individual LEDs is poor, leading to lack of uniformity of the illuminated area. Also, the uniformity of the light produced by the individual LEDs is poor, and even after they mix on the target, the resulting uniformity is poor, perhaps ±25%.

Another disadvantage is that the overall brightness of the illumination is limited by the packing density of the individual packaged LEDs, which are typically housed in 5 mm or 3 mm diameter acrylic packages. For example, a 30 mm diameter ring of 5 mm LEDs can only hold about 16 of these lensed LEDs.

In order to produce a shorter working distance it has been proposed to arrange the LEDs at an angle to the optical axis. This means that the illuminator works well at a particular working distance, which is determined by the position at which the beams from the individual LEDs coincide. However, there is no facility for adjusting the working distance.

U.S. Pat. No. 5,822,053 describes a system for improving the uniformity and for matching the angle of illumination with the field of view. This consists in essence of bending the metal legs on the individual packaged LEDs to adjust the orientation of the beam from each LED. By observing the pattern on the target plane, it can then be ensured that the uniformity is improved to the extent that is possible, given the non-uniformity of the individual LEDs to start with. Following adjustment, the LED packages are fixed in place with epoxy. This technique can only improve uniformity up to a point, and does not address the other fundamental limitations of using a ring of lensed LEDs, such as limitations of brightness, compactness, and scaleability to small sizes.

U.S. Pat. No. 5,580,163, describes a mechanical adjusting system to enable the angle of incidence of the illumination from a ring illuminator consisting of the lensed LEDs to be varied. This is mechanically complex, and adds significantly to the manufacturing cost of the system and to its volume and mass. Also, it does not address uniformity and brightness problems.

Use of annular lenses has been described in the prior art. U.S. Pat. No. 4,567,551 describes a multidirectional surface illuminator which uses a Fresnel lens to redirect and focus the light from the light sources arrayed around the outside of an illuminator housing, so as to illuminate the object under inspection from a particular quadrant of the illuminator. It is very difficult to make a compact illuminator using this technique due to the arrangement of the light sources outside of the housing. Additionally, this arrangement does not achieve a desirable level of uniformity over a target area, and is not suitable for extension to very small sizes.

U.S. Pat. No. 5,690,417 describes a surface illuminator with a means for adjusting the orientation and inclination of the incident illumination, which includes light emitting diodes arranged in coaxial circles. Each coaxial circle of diodes may have their beam angles inclined at different angles to the angle of the axis of the housing. The diodes are energizable in pie-shaped sectors so that arcuate clusters of diodes may be illuminated to enable the orientation of the resultant illumination to be varied. The light emitting diodes are individually packaged so as to include a collimating lens and a Fresnel lens is used to focus and redirect the light towards the illuminated object. The illumination is similar to the prior art illuminator illustrated in FIG. A from the perspective of efficiency and uniformity. The only function of the Fresnel lens is to enable the variation of the angular inclination from the various segments, while using light emitting diodes mounted coaxially with the housing.

U.S. Pat. No. 5,897,195 describes an illuminator with a cylindrical or conical array of light emitting diodes producing collimated light beams that are redirected towards the illuminated object by a Fresnel-like diffuser. Again, this is a variation of the prior art illuminator shown in FIG. A which might have some advantages for producing particular angular inclinations. However, it is not very suitable for compactness, high uniformity or high efficiency.

These disadvantages with using discrete light sources such as LEDs have led to use of large illuminators for machine vision systems and for microscopy in order to achieve the required illumination intensity and distribution. These illuminators may, for example, comprise a ring-shaped fluorescent tube. These units are bulky and so impose design limitations on the instrument with which they are intended to be used, and they also are not efficient for producing monochromatic light. These illuminators may also comprise "cold light" sources, consisting of a fan-cooled halogen bulb providing light via a light pipe and adapter, which are bulky and expensive.

Therefore, it is an object of the invention to provide a ring illuminator which has some or all of the following advantages:

- is compact, providing a high ratio of brightness to illuminator volume,
- may have a size within a large range extending down to a compact size, for example an illuminator having 10 LEDs with a housing diameter of less than 10 mm,
- provides a uniform illumination intensity over the desired target area,
- incorporates redundancy so that failure of some sources does not result in darker areas within the illuminated area,
- has a relatively high optical efficiency,
- can be readily focused to adjust the size of the illuminated area,
- allows configuration for a required application at the design and manufacturing stages in a versatile manner.

SUMMARY OF THE INVENTION

According to the invention, there is provided an illuminator comprising a plurality of light sources mounted in a ring configuration, and an optical system for directing light from the light sources onto a target plane, characterised in that, the properties of the optical system and the spatial arrangement of the optical system with respect to the light sources is such that light emitted by the light sources mixes to uniformly illuminate the target plane.

Thus, the optical system properties and the spatial arrangement achieve uniformity—desirable for many industrial applications—in an efficient manner without the need for a large single light source such as a fluorescent bulb.

In one embodiment, the optical system comprises an annular lens. This is a very simple, compact, and effective optical system.

In one embodiment, the separation of the light sources and the lens is less than the lens focal length. This achieves a uniform illumination area which is greater than the area encompassed by the lens, and also achieves excellent spread in the radial direction.

In one embodiment, the lens comprises means for controlling spread in the radial direction sufficient for uniformity and adequate illumination intensity across the target plane.

In one embodiment, the effective diameter of the ring of light sources is greater than that of the lens by 2% to 10%. This helps to control the size of the illuminated area and to achieve excellent uniformity.

In one embodiment, the lens comprises means for allowing light from the light sources to spread primarily in the tangential direction so that any point on the target plane is illuminated by at least 25% of the light source. This is a very simple way of achieving uniformity and excellent brightness on the target plane.

In one embodiment, the light sources comprise means for emitting uncollimated light. This also contributes to spread of light, helping to achieve uniformity.

In one embodiment, each light source is a semiconductor die. This is a compact arrangement.

In one embodiment, the illuminator comprises a housing supporting the light sources and the optical system, said housing having a chamber for the light sources and a chamber for the optical system. This provides robustness and reliability.

In one embodiment, the light source chamber supports the light sources in efficient thermal contact with the housing. This contributes to reliability.

In one embodiment, the housing supports the optical system in a manner whereby it is accessible for adjustment by users. This allows excellent versatility.

The annular lens may have a Fresnel pattern, and preferably the Fresnel pattern comprising means for correcting for spherical aberration. The lens may alternatively comprise a diffraction pattern. The lens may have a convex shape on one side and be flat on the other side. The lens may comprise a plurality of individual lenses arranged in an annular configuration.

In one embodiment, the light sources are mounted on a circuit board. This both allows simple electronic control and provides mechanical support.

The circuit board may have electronic components to control or switch current to the light sources.

In one embodiment, the circuit board is flexible and is formed into a ring. This provides ease of manufacture.

In one embodiment, the drive circuits comprise means for providing different colour illumination. In another embodiment, the drive circuits comprise means for driving rings of light sources of different radii to electrically vary angle of illumination. These features provide excellent versatility and simple control.

In one embodiment, the circuit board comprises a plurality of separate circuits. In another embodiment, each circuit drives light sources mounted in a pattern whereby failure of a circuit has a uniform impact across the target plane. These features provides excellent fault-tolerance.

In one embodiment, the light sources are covered by epoxy, preferably applied in a continuous layer.

The epoxy layer may contain phosphorescent material.

In one embodiment, the optical axis of the lens cross-section is inclined at an angle to the normal to the plane of the annulus.

In one embodiment, the lens is inclined at 90° to the normal to the plane of the annulus.

In one embodiment, the lens is of a deformable material.

In one embodiment, the lens has a flat arc-shaped starting configuration before being bent into an overall ring configuration in plan.

According to another aspect, the invention provides a method of producing an illuminator comprising a plurality of light sources mounted in a ring configuration and an annular lens for directing light from the light sources onto a target plane, wherein, the annular lens is chosen to have properties such that the lens mixes light from different light sources in the tangential direction and controls spread in the radial direction so that a target plane at a desired working distance is uniformly illuminated, and the separation of the lens from the light sources, and the light source ring diameter: lens diameter ratio are chosen to set the desired illumination area.

In one embodiment, the light source ring diameter: lens diameter ratio is chosen within a range of 1.02 to 1.10.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which.

Figure 1:
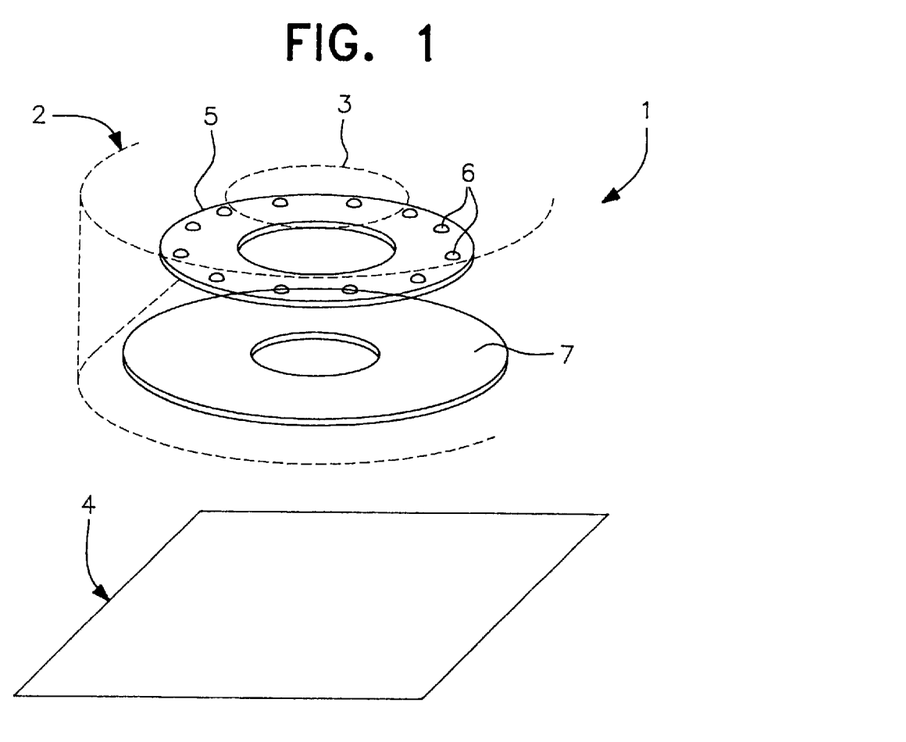
FIG. 1 is a diagrammatic perspective view of a ring illuminator of the invention.
Figure 2:
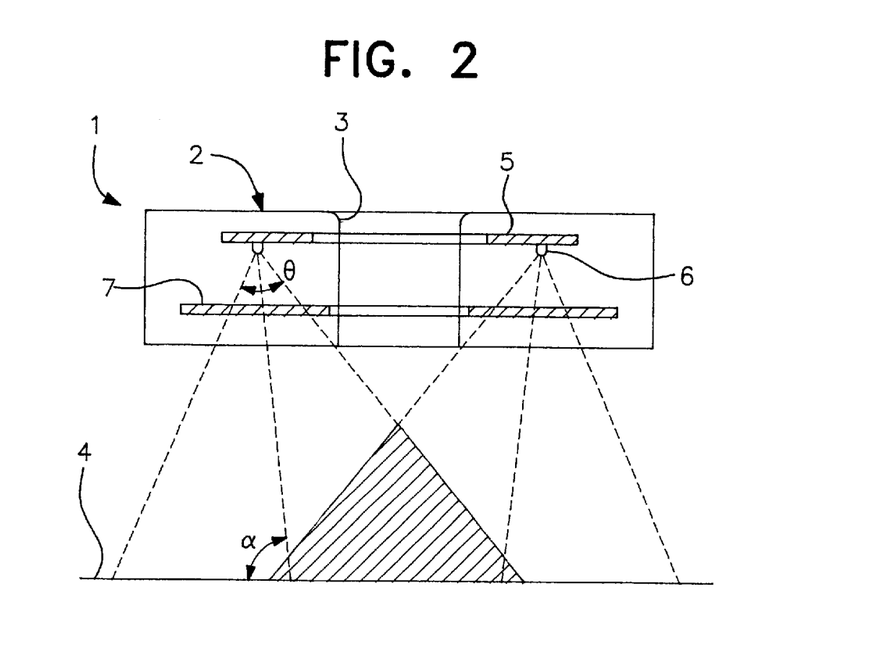
FIG. 2 is a cross-sectional view of the illuminator of FIG. 1, showing spread of light from the light sources.

Referring to FIGS. 1 and 2 a ring illuminator 1 comprises a housing chamber 2 having a central opening 3 for a camera field of view. The illuminator 1 is for uniform illumination across a target plane 4.

The illuminator 1 comprises an annular printed circuit board 5 supporting a ring of LEDs 6. An optical system, in this embodiment an annular Fresnel lens 7, is mounted beneath the LEDs 6.

Referring to FIG. 2, the properties of the lens 7 and the spatial arrangement of the lens 7 with respect to the LEDs 6 is such that light emitted by the LEDs mixes to uniformly illuminate the target plane 4. The lens 7 spreads the light extensively in the tangential direction, perpendicular to the plane of the page. This achieves comprehensive mixing of the light. The following aspects of the spatial arrangement also contribute to uniformity across the target plane.

The separation between the LEDs 6 and the lens 7 is less than the focal length of the lens 7.

The effective diameter of the LEDs 6 is slightly greater (by 2%) than that of the lens 7. In general it has been found that if the LED effective diameter is greater than the lens effective diameter by a value in the range 2% to 10% there is particularly good distribution of light in the radial direction. Choice of this ratio sets the value for $\alpha$, the angle of incidence of the illumination on the target plane.

The viewing angle, $\theta$, of the LEDs 6, is partly dependent on the lens/LED separation.

Other factors such as the physical size of the lens and the presence or absence of restrictive apertures in the housing.

A combination of these aspects achieves the desired uniformity across the target plane with excellent efficiency and compactness. It is possible that the lens/LED separation be greater than the lens focal length, in which case the lens/LED diameter ratio is chosen to ensure sufficient mixing and uniformity for the illumination area on the target plane 4.

The spatial arrangement and the lens properties achieve uniform mixing of the light to the extent that at any point on the target plane light is received from at least 25% of the LEDs 6 in various proportions.

The angle of incidence of the illumination on the target plane (indicated as $\alpha$) may be electronically varied if the illuminator has a plurality of rings of LEDs, in which case choice of a particular ring to be activated sets the value for $\alpha$.

The LEDs 6 emit uncollimated light, again contributing to uniform illumination.

Figure 3A:
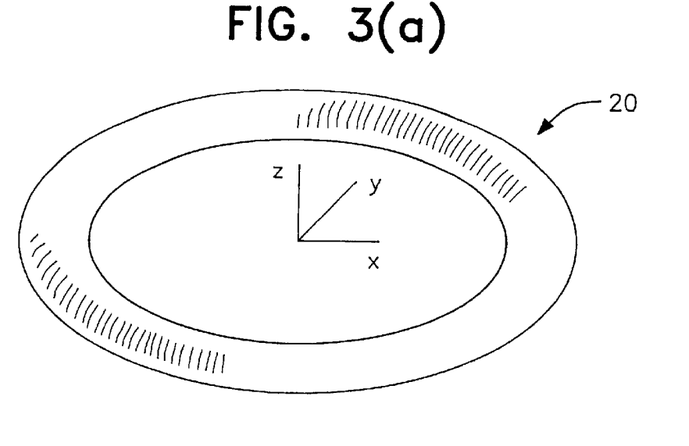
FIG. 3(a) is a perspective view of an annular lens.
Figure 3B:
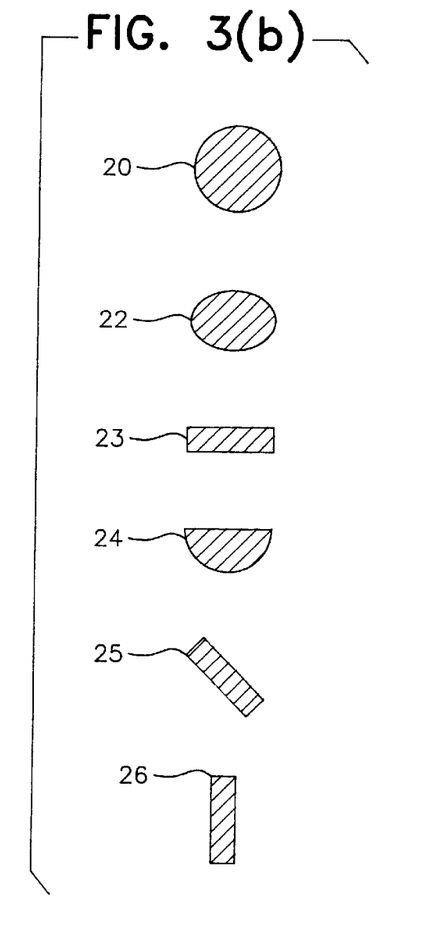
FIG. 3(b) is a set of sample cross-sections.

Referring to FIG. 3(a) an annular lens 20 of circular cross-section may be used. The lens has rotational symmetry about the z-axis, as shown. As shown in FIG. 3(b) the cross-sectional shape (in the x–z plane) may be:

22—bi-convex,
23—Fresnel (as for the illuminator 1 of FIGS. 1 and 2),
24—combined Fresnel and refractive,
25—Fresnel, tilted with respect to the Z axis
26—Fresnel, orthogonal to the Z axis Other shapes which achieve uniformity across the target plane may also be used.

Figure 3C:
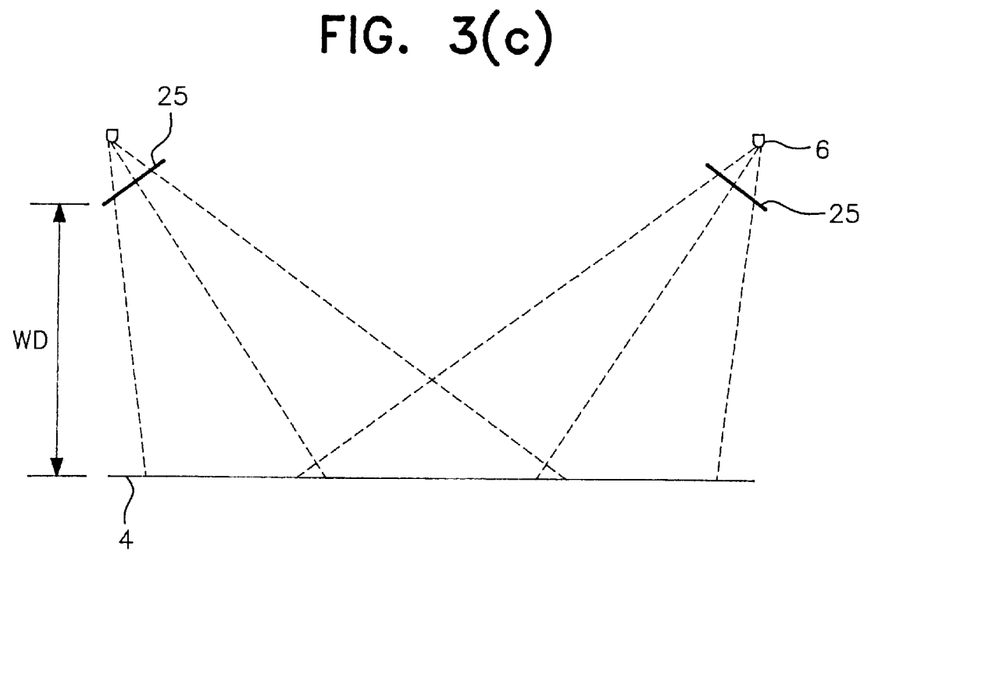
FIGS. 3(c) and 3(d) are views illustrating illumination arising from different lenses.

Referring to FIG. 3(c) operation of an illuminator with the lens 25 is shown. The target 4 is illuminated by the annular Fresnel lens 25 which is orientated in elevational view in a manner whereby it extends at an angle of approximately 45° to the (horizontal) plane of the target, particularly for relatively short working distances. The lens may be orientated up to 90°, as shown for the lens 26 in FIG. 3(d). This is particularly effective for even shorter working distances or for "dark-field" applications requiring illumination from low angles of incidence. The lenses 25 and 26 may be deformable because of choice of material or thickness. The starting configuration when the material lies flat may in this case be arc-shaped. Alternatively, the lens may be formed in rigid material by various casting or moulding techniques.

Figure 4:
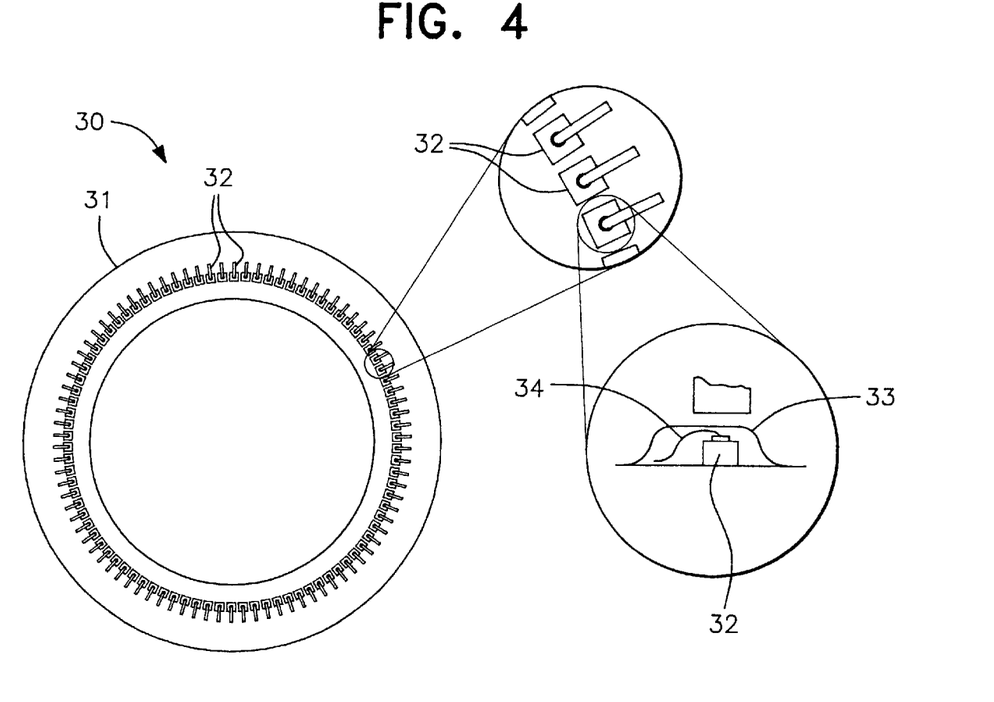
FIG. 4 is a plan view of LEDs on a printed circuit board together with a detailed view showing encapsulation of a single LED.

Referring to FIG. 4 a light source assembly 30 for an illuminator is illustrated. The assembly 30 comprises a board 31 supporting LED chips 32 encapsulated by epoxy resin 33 and connected to the circuit by wire bonds 34. The separation between the chips is in this embodiment 0.50 mm. As chip volume is small, the overall volume of the illuminator is small. In this case the radius on which the chips are located is only 8 mm.

Figure 5A:
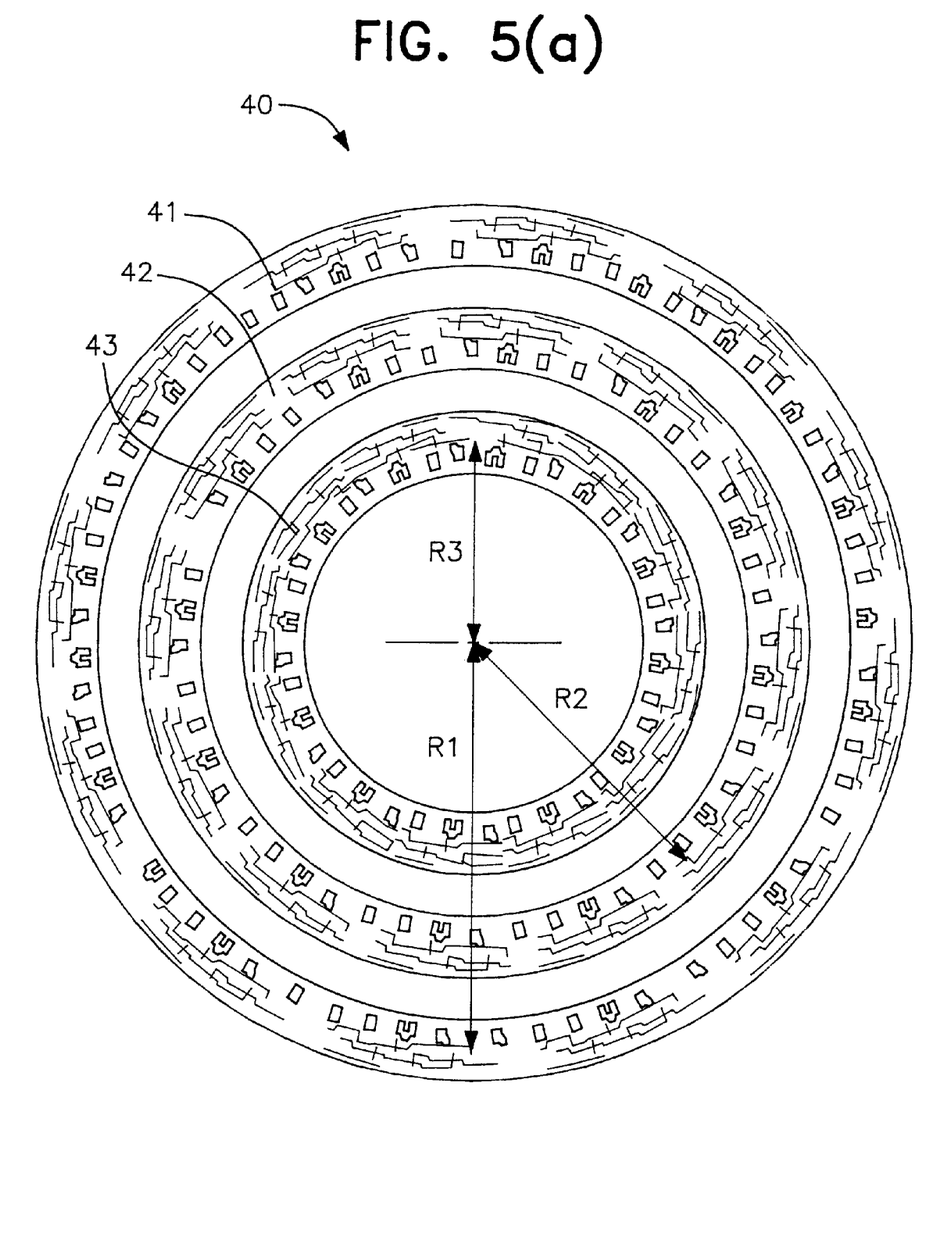
FIG. 5(a) is a plan view showing the arrangement of LEDs in an alternative illuminator.
Figure 5B:
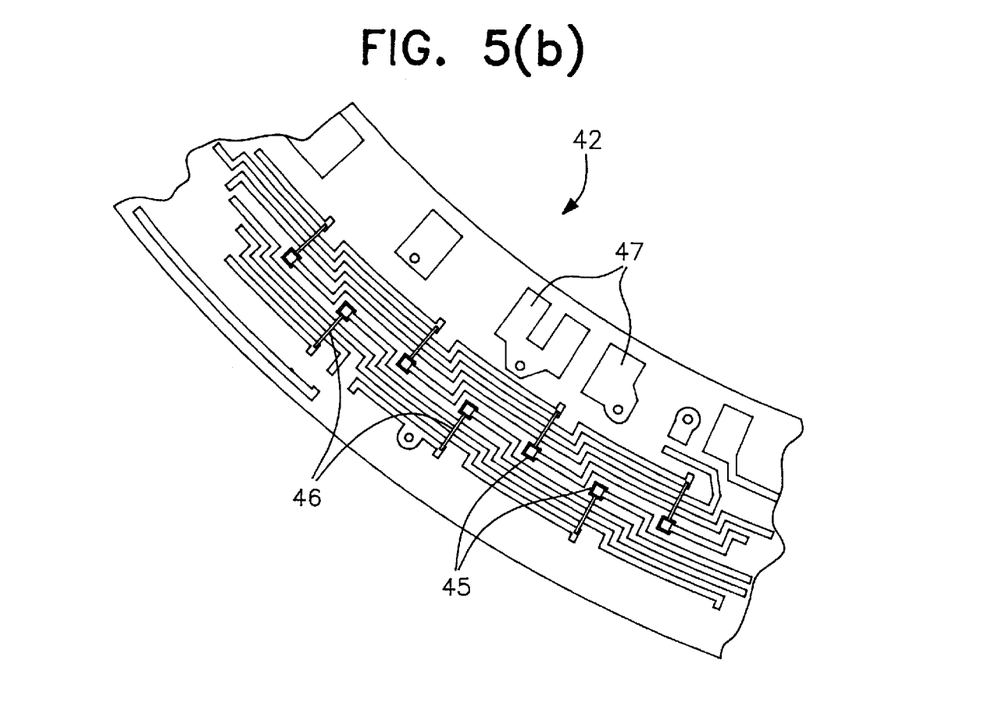
FIG. 5(b) is a more detailed view of the circuits of the illuminator of FIG. 5(a)

As described above, the LEDs can be arranged in separate rings, each at a different effective angle with respect to the centre of curvature of the annular lens, so that the working distance of the light source assembly 40 can be adjusted electrically, by energising an alternative ring of diodes. This is illustrated schematically in FIG. 5(a), in which LEDs are on separate circuits 41, 42, and 43 of radii R1, R2, and R3, corresponding to different values of α as defined in FIG. 2. Referring to FIG. 5(b), each circuit comprises LED chips 45 in a semiconductor die connected to a circuit by wire bonds 46. Pads 47 are provided for mounting other components such as resistors or transistors. Also, each ring may have chips with a different colour of illumination so that colour choice or mixing may be electronically driven.

If other factors are unchanged, the area which is illuminated is determined by how close the light sources are to the annular lens. The illuminated area widens as this distance is reduced. This is taken into account in the physical design of the housing. The housing can be either designed so as to provide the appropriate width of illumination at the required working distance, or else it can include a simple mechanical adjustment which enables adjustment of the source to lens separation, and thus adjustment of the area of illumination.

Figure 6:
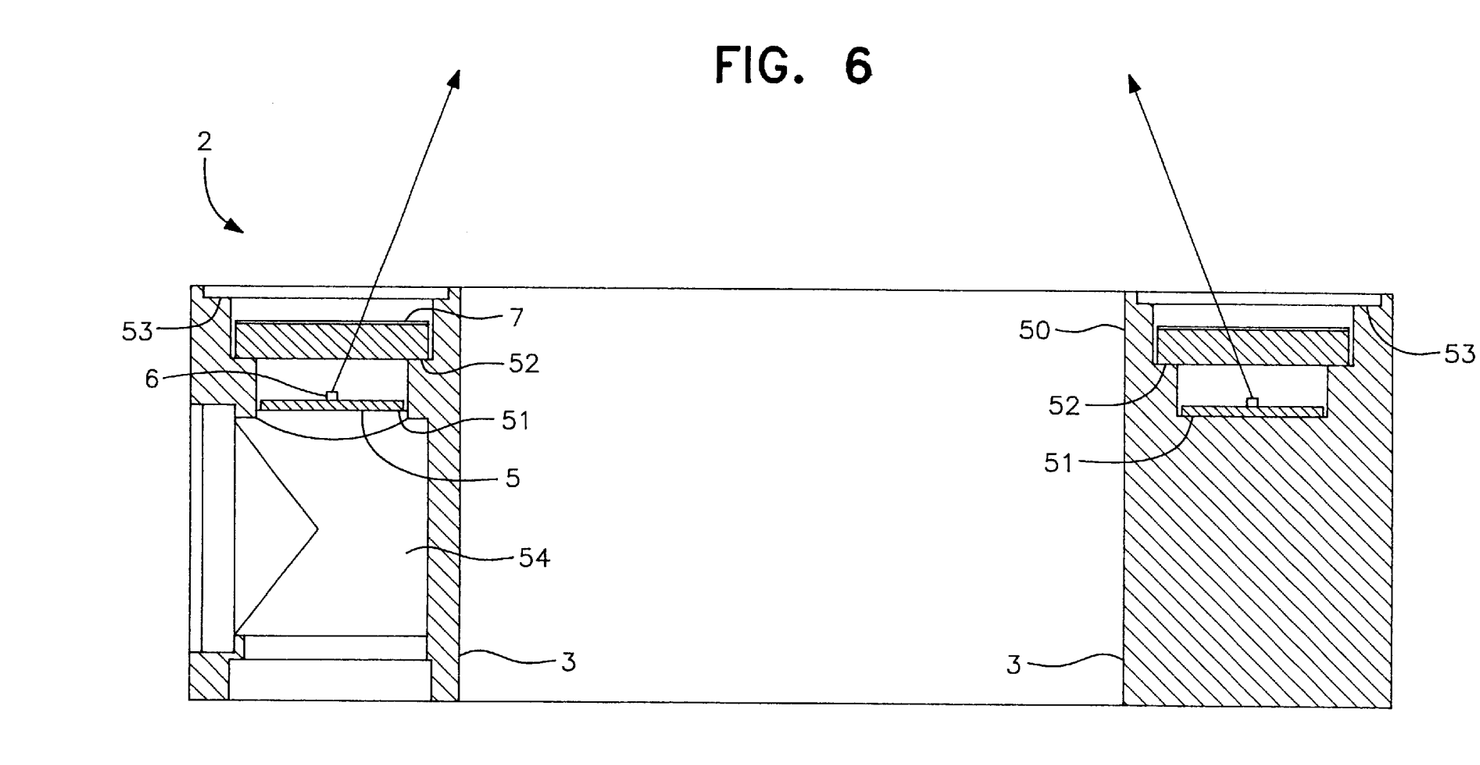
FIG. 6 is a cross-sectional view of a housing of the illuminators of FIGS. 1 to 5 inclusive.

Referring to FIG. 6, the housing 2 of FIG. 2 is shown in detail. The body 50 is of solid aluminum construction, as shown on the right side of FIG. 6. The housing 2 comprises a seat 51 for the PCB 5, a seat 52 for the lens 7, and a further seat 53 for a diffractor or additional lens, if required. The housing 2 also comprises an opening 54 for access of cables to the PCB 5. This arrangement allows excellent heat dissipation from the PCB 5 by conduction through the body of the housing 2. The construction is also very robust and compact. The housing may be modified to incorporate a threaded fitting having the lens seat so that the LED-lens distance may be easily adjusted, or the lens may be replaced easily for different operating conditions. It is envisaged that the lens may be repositioned by an electromechanical mechanism for configuration for different applications.

Figure 7:
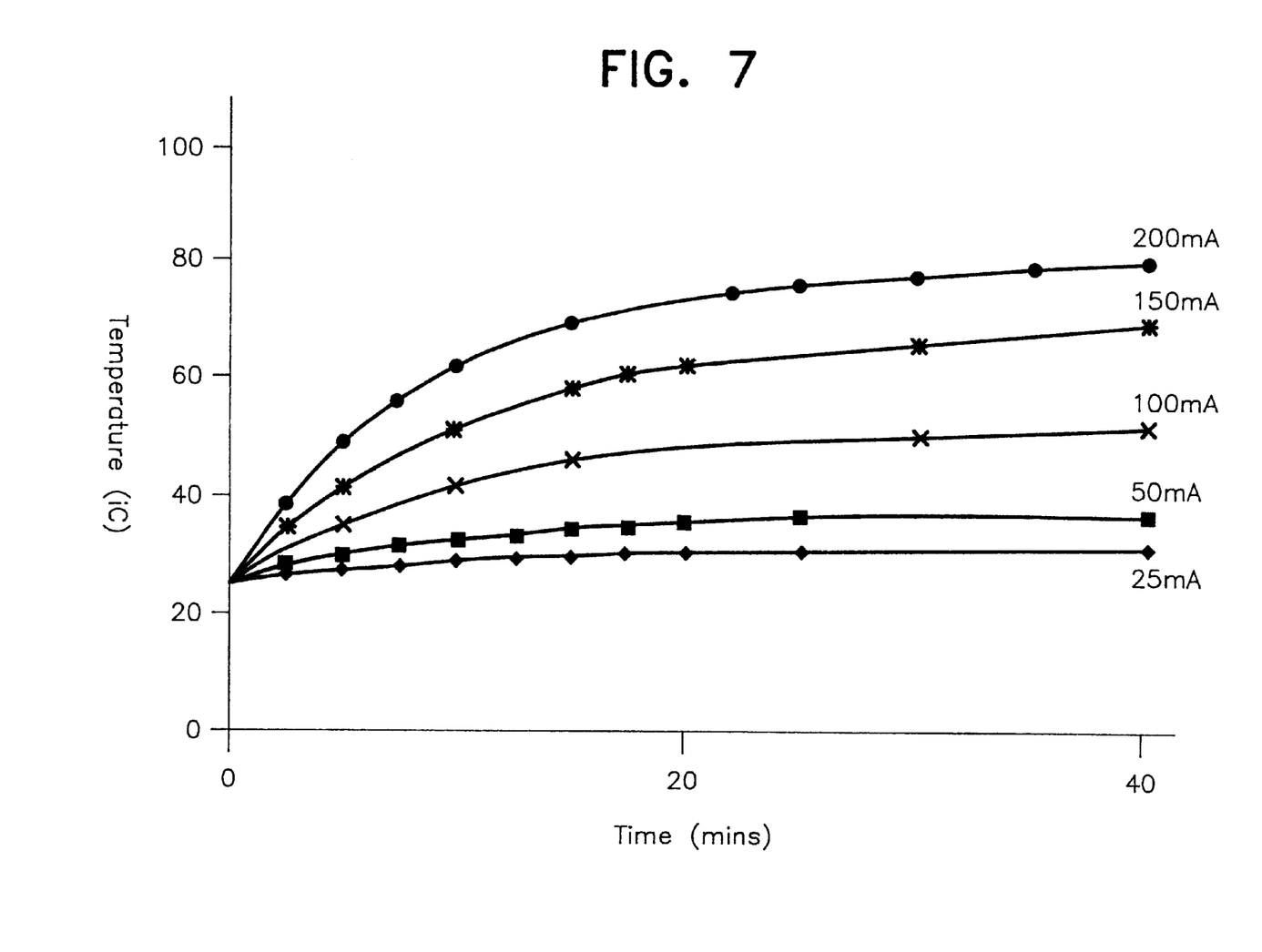
FIG. 7 is a plot illustrating housing temperature versus driving current characteristics of the illuminator.

The housing 2 provides excellent conductive heat dissipation, the importance of which is clear from consideration of the profiles of FIG. 7. This plot illustrates the case temperatures which are achieved by an illuminator of the invention containing 100 LED chips, which is placed on at thermally insulating surface at an ambient temperature of 22° C. These chips are arranged in 10 parallel circuits, each containing 10 light emitting diodes connected in series. Thus the current of 200 mA corresponds to 20 mA going through each chip, which is the recommended continuous current rating of these particular chips. Due to the inefficiencies of the conversion of electrical power to light power within each chip, most of the electrical power which is being supplied to the circuit is being dissipated as heat, and this heat causes the temperature of the housing to increase, as indicated in the diagram. By selecting the materials used in the circuit board and in the housing, and in the manner used to connect the board to the housing, and in the physical size, mass and shape of the housing the amount of temperature rise can be controlled. These issues must be carefully addressed, especially in using the particular advantage of this invention to use a densely packed array of sources in a physically small housing. Because, as can be seen from FIG. 6 the LED chips can be mounted in excellent thermal contact to the metal housing, it is a relatively simple matter to provide adequate heat-sinking for the housing to maintain a cool operating temperature of the LED chips, say less than 50° C. as required for reliable operation.

A particular advantage of the invention is its mechanical simplicity and compactness. The circuits shown in FIG. 5 are designed to contain 100 light emitting diode chips or packages. The illuminator may be smaller especially when using light emitting diode chips, which are typically only 0.25 mm square.

Figure 8A:
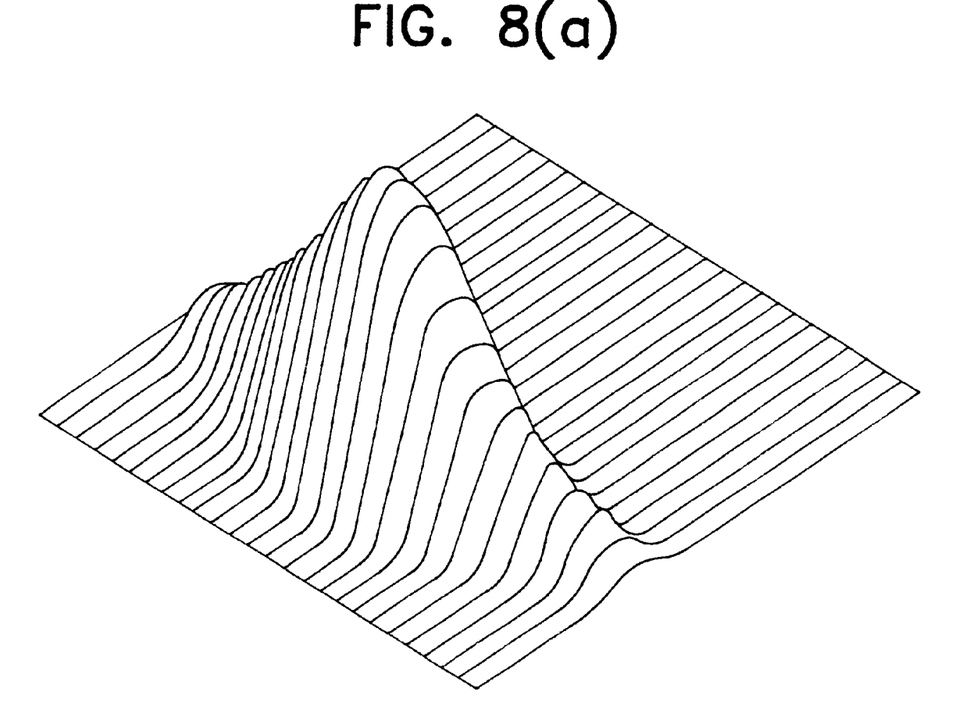
FIG. 8(a) is a 3-D plot illustrating the distribution of light on a target plane from a single LED in the illuminator and FIG. 8(b) is a 3-D plot illustrating total distribution on a target plane from 100 equi-spaced LEDs arranged in a ring in the illuminator.

An important feature of the invention is how well the light from the various light emitting diodes mixes on the target plane through the action of the annular lens on the light as it passes through it. This is illustrated in FIG. 8(a), which is a computer-based "Monte Carlo" simulation showing the pattern on the target plane from a single 0.3 mm square LED chip located on the source circuit with a housing of FIG. 6. The light is spread into a fuzzy segment of an arc. Clearly, in an illuminator containing a number (for example 100) of LEDs, arranged in a ring, when viewed from a point on the target plane, the light at that point will appear to come from many separate diodes, so that it will be very uniform in intensity and colour. This is due to the mixing effect, which normally exist from chip to chip.

Figure 8B:
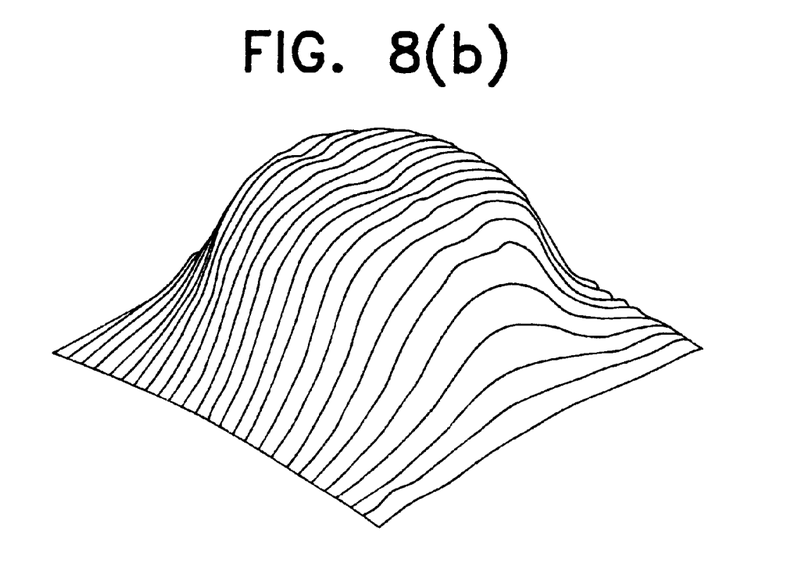

Referring to FIG. 8(b) there are illustrated simulations of a 100 chip illuminator in which all of the chips are illuminated, for a working distance of 100 mm. These are two dimensional plots of the relative intensity of the light hitting the target plane in a 100 mm square box, from an illuminator in which the diameter of the circle of light emitting diode sources is 37 mm. The illuminator is designed so that at the desired working distance the uniformity and brightness are optimised. Experimental tests revealed that these simulations are accurate to ±10%.

Figure 9:
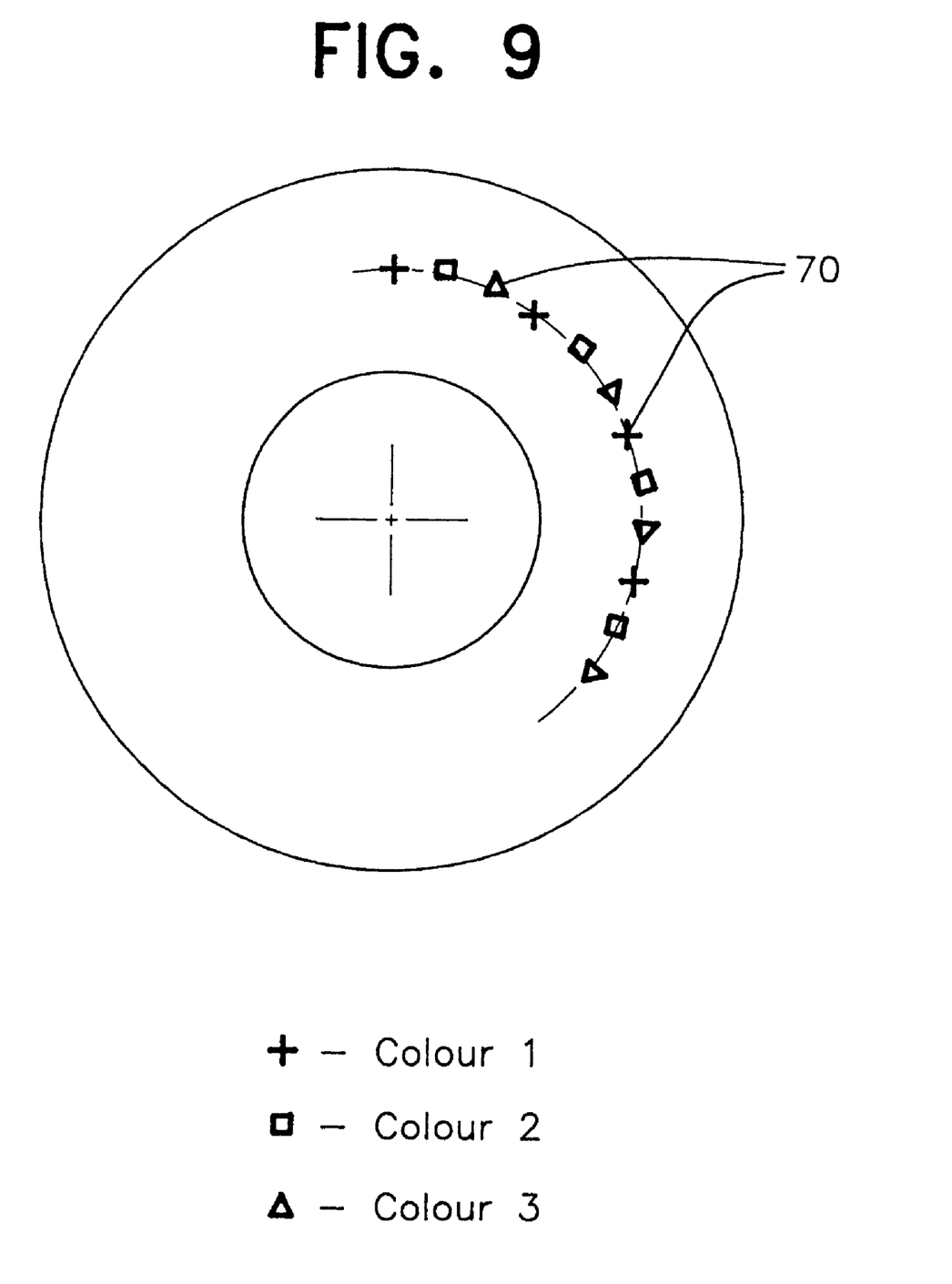
FIG. 9 is a plan view of an LED configuration in which there is a single ring of different coloured LEDs.

As shown in FIG. 9, LED chips 70 may be arranged in separate circuits, with LEDs of different colours in each circuit so that the colour of the uniformly illuminated area may be sequentially changed by turning on only one LED circuit at a time. Also, different circuits may be simultaneously electrically driven by different currents so that the colour of the resulting illuminated area can be adjusted and, for example, can be made white. It has been found that mixing of R (color 1), G (color 2), and B (color 3) coloured LEDs achieves excellent quality white light, which is particularly important for microscopy applications. Excellent quality white illumination may also be achieved using a mix of blue LEDs together with a phosphor, which may for example be contained in the LED-encapsulating epoxy.

The invention can also produce illuminated areas which are not rotationally symmetric, for example rectangular, by arranging the LED chips appropriately in the plane of the PCB.

The LED chips can be individual unpackaged LED chips, which are typically about 0.25 mm square. They could also be chips in surface mount packages. The chips could also be so-called micro-cavity LEDs with a narrower spectral distribution than normal LEDs. The chips could also be laser diode chips, especially vertical cavity surface-emitting lasers (VCSELs) whose geometry is especially suitable for PCB mounting as described above. They could also be chips in individually lensed packages, such as described above.

Figure 3D:
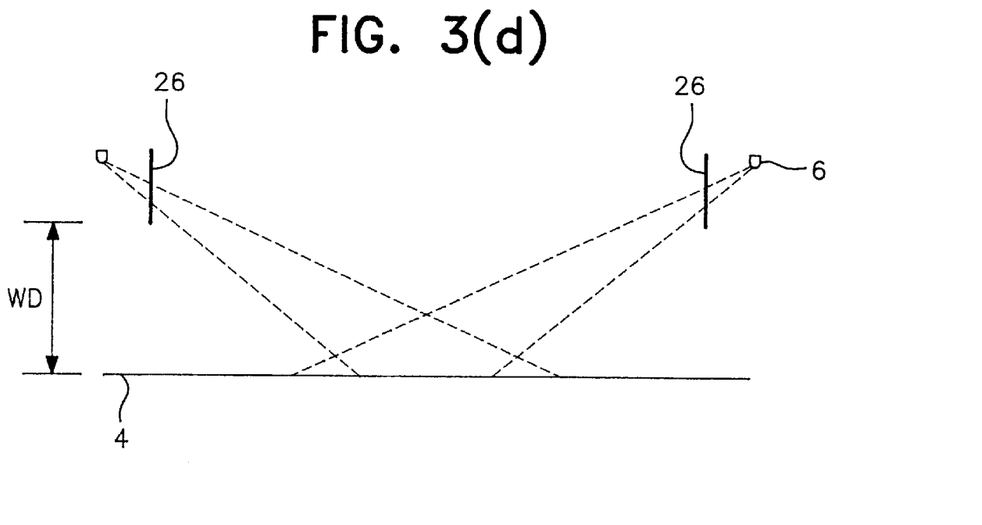

The PCB may be made from FR4, or alternatively from ceramic or other high-thermal conductivity material which would be advantageous if a lot of optical power is desired. The operating temperature of the chips may be maintained at a satisfactory temperature, either in isolation or with passive cooling by a heat sink for example, or actively cooled by a Peltier device. Alternatively, a combination of such approaches may be used. The use of a flexible PCB would be particularly advantageous for applications as shown in FIGS. 3(c) and 3(d).

The annular lens can have a variety of shapes as described above referring to FIG. 3. It can be a toroidal-shaped piece of acrylic, polycarbonate, glass, or other special material, having a generally circular cross-section at any point along the annulus. It could have a completely flat surface on one side, so that the cross-section is plano-concave or plano-convex. Very advantageous for compactness is the use of a Fresnel surface, so that the annulus is a flat ring in shape, with Fresnel refracting rings on one or both surfaces to provide the focussing properties which are required. These Fresnel features can be designed so as to correct for spherical aberration, or in other ways to improve the properties of the illumination on the target surface, such as sharpness or uniformity. The annular ring could be made with an essentially flat ring as described above, but which has diffractively-patterned surfaces designed to provide the required focussing properties. This would be especially useful in the case where laser chips are in use as sources on the PCB, due to the narrow spectral spread of a laser, which is especially suitable for diffractive optics. The annular ring could have a convex shape on one side and a flat surface on the other side could have a Fresnel or diffractive pattern on it.

The chips on the PCB may be arranged in different circuits, insofar as possible to facilitate the correct current driving conditions, or to make it possible to have different colours illuminating the target at the same or different times, or so as to make it possible to have different effective working distances, or to minimise the reduction in uniformity if some circuits fail. The board may also contain voltage dropping resistors, as well as other circuitry for strobing the chips, if required, or for controlling the circuits. The changing of the illumination pattern of the light head could thus be implemented in various ways—either by opening the housing and making an on-board adjustment to the circuitry, or by having the circuits connected to electrical switches on the housing, or by electrical circuitry which can be controlled externally to the light head. Because of the dense arrangement of sources, the invention enables a variety of failure-tolerant features as follows. The sources can be arranged in separate circuits, in which the sources in each circuit are interleaved with sources in other circuits. For example, a 100 chip illuminator might have 100 circuits of 10 chips each in which the $1^{st}, 11^{th}, 21^{st} \ldots$ chips along the circumference are in the same circuit, the $2^{nd}, 12^{th}, 22^{nd} \ldots$ chips are in the next circuit, and so on. The effect of a circuit failure would thus be to reduce overall brightness by 10% rather than to produce a dark area in the illumination.

It will be appreciated that the invention provides an illuminator which is compact, has a low power consumption, and which achieves excellent illumination uniformity. The invention also provides these properties for short or long working distances and so allows excellent versatility for the range of applications which benefit. The illuminator of the invention is particularly suitable for industrial instruments such as used in microscopy or machine vision applications because of the above properties. The illuminator design is scaleable. Another advantage is excellent colour control, as it can provide single colour, switched R, G, or B colour, or combined RGB white illumination.

The invention is not limited to the embodiments described but may be varied in construction and detail. For example, the annular lens may comprise a number of discrete lens arranged in an annular configuration. Also, the illuminator may not have a through hole as applications such as backlighting do not require it. It is also envisaged that the optical system may comprise an annular reflector instead of a lens. The board need not necessarily be annular even where the housing has a through hole. It may, for example be square in outline plan. It is also envisaged that a particularly compact embodiment of the invention could be achieved by having all of the sources and associated circuitry integrated onto a single monolithic optoelectronic integrated circuit. By appropriate choice of semiconductor, dielectric deposition and patterning techniques the complete illuminator (including optics and housing) could be monolithically integrated.

What is claimed is:

1. An illuminator comprising
a plurality of light sources mounted in a ring configuration, and
an optical system spaced from the plurality of light sources for directing light from the light sources onto a target plane,
the optical system including an annular lens mounted to mix light from all of the plurality of light sources and uniformly illuminate the target area, and
the properties of the optical system and the spatial arrangement of the optical system with respect to the plurality of light sources is such that the light emitted by the plurality of light sources is mixed tangentially, and radial spread of the light is controlled, to uniformly illuminate the target plane over an area at least equal to that encompassed by the ring of light sources and the illumination extending uniformly from a center to a periphery of the target plane.

2. An illuminator as claimed in claim 1, wherein a separation of the light sources and the lens is less than a focal length of the lens.

3. An illuminator as claimed in claim 1, wherein an effective diameter of the ring of light sources is greater than an effective diameter of the lens by 2% to 10%.

4. An illuminator as claimed in claim 1, wherein the light sources comprise means for emitting uncollimated light.

5. An illuminator as claimed in claim 1, wherein each light source is a semiconductor die.

6. An illuminator as claimed in claim 1, wherein the illuminator comprises a housing supporting the light sources and the optical system, said housing having a chamber for the light sources and a chamber for the optical system.

7. An illuminator as claimed in claim 6, wherein the light source chamber supports the light sources in thermal contact with the housing.

8. An illuminator as claimed in claim 1, wherein the annular lens comprises a Fresnel pattern.

9. An illuminator as claimed in claim 8, wherein the Fresnel pattern is configured for correcting for spherical aberration.

10. An illuminator as claimed in claim 1, wherein the lens comprises a diffraction pattern.

11. An illuminator as claimed in claim 1, wherein the annular lens has a convex shape on one side and is flat on the other side.

12. An illuminator as claimed in claim 1, wherein the lens comprises a plurality of individual lenses arranged in an annular configuration.

13. An illuminator as claimed in claim 1, wherein the light sources are mounted on a circuit board.

14. An illuminator as claimed in claim 13, wherein the circuit board has electronic components to control or switch current to the light sources.

15. An illuminator as claimed in claim 13, wherein the circuit board is flexible and is formed into a ring.

16. An illuminator as claimed in claim 13, wherein the light sources provide different colour illumination.

17. An illuminator as claimed in claim 13, wherein the drive circuits comprise means for driving rings of light sources of different radii to electrically vary angle of illumination.

18. An illuminator as claimed in claim 13, wherein the circuit board comprises a plurality of separate circuits.

19. An illuminator as claimed in claim 18, wherein each circuit drives light sources mounted in a pattern.

20. An illuminator as claimed in claim 1, wherein the light sources are covered by epoxy.

21. An illuminator as claimed in claim 20, wherein the light sources are covered by a continuous epoxy layer.

22. An illuminator as claimed in claim 21, wherein the epoxy layer contains phosphorescent material.

23. A ring illuminator as claimed in claim 1, wherein the optical axis of the lens cross-section is inclined at an angle to the normal to the plane of the annulus.

24. A ring illuminator as claimed in claim 23, wherein the lens is inclined at 90° to the normal to the plane of the annulus.

25. A ring illuminator as claimed in claim 1, wherein the lens is of a deformable material.

26. A ring illuminator as claimed in claim 25, wherein the lens has a flat arc-shaped starting configuration before being bent into an overall ring configuration in plan.

27. A method of producing an illuminator comprising the steps of:

mounting a plurality of light sources in a ring configuration, positioning an annular lens for directing light from the plurality of light sources onto a target plane, choosing the annular lens to have properties such that the lens mixes light from different light sources in the tangential direction and controls spread in the radial direction so that a center to a periphery of the target plane at a desired working distance is uniformly illuminated, separating the lens from the light sources by a predetermined distance, and choosing the light source ring diameter to lens diameter ratio to set a desired illumination area of the center to the periphery of the target plane.

28. A method as claimed in claim 27, wherein the light sources ring diameter: lens diameter ratio is chosen within a range of 1.02 to 1.10.

* * * * *